US008450293B2

(12) United States Patent
Jones et al.

(10) Patent No.: US 8,450,293 B2
(45) Date of Patent: May 28, 2013

(54) SYNTHESIS AND CHARACTERIZATION OF C8 ANALOGS OF C-DI-GMP

(75) Inventors: Roger A. Jones, Martinsville, NJ (US); Elizabeth Veliath, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1 day.

(21) Appl. No.: 13/207,169

(22) Filed: Aug. 10, 2011

(65) Prior Publication Data

US 2012/0041057 A1 Feb. 16, 2012

Related U.S. Application Data

(60) Provisional application No. 61/372,169, filed on Aug. 10, 2010.

(51) Int. Cl.
| | | |
|---|---|---|
| *A01N 43/04* | (2006.01) | |
| *A61K 31/70* | (2006.01) | |
| *C07H 19/00* | (2006.01) | |
| *C07H 19/04* | (2006.01) | |
| *C07H 19/20* | (2006.01) | |

(52) U.S. Cl.
USPC ............... 514/48; 514/43; 514/45; 536/26.1; 536/26.11; 536/26.12; 536/26.3; 536/26.5; 536/26.72

(58) Field of Classification Search
None
See application file for complete search history.

(56) References Cited

U.S. PATENT DOCUMENTS

| | | | |
|---|---|---|---|
| 7,709,458 B2 * | 5/2010 | Karaolis et al. | .................. 514/45 |
| 2012/0178710 A1 | 7/2012 | Jones et al. | |

FOREIGN PATENT DOCUMENTS

| | | |
|---|---|---|
| WO | WO 2005/030186 | 4/2005 |
| WO | WO 2006/045041 | 4/2006 |
| WO | WO 2011/003025 A1 | 1/2011 |

OTHER PUBLICATIONS

Amiot et al., "New Approach for the Synthesis of c-di-GMP and Its Analogues", *Synthesis*, 24, 4230-4236, (2006).
Asadi et al., "G∧ C Quartet—A DNA-Inspired Janus-GC Heterocycle: Synthesis, Structural Analysis and Self-Organization", *J. Am. Chem. Soc.*, 130, 12860-12861, (2008).
Ching et al., "Synthesis of cyclic di-nucleotidic acids as potential inhibitors targeting diguanylate cyclase", *Biorg. Med. Chem.*, 18, 6657-6665, (2010).
Cho et al., "$^{15}$N Nuclear Magnetic Resonance Studies on the Tautomerism of 8-Hydroxy-2'-deoxyguanosine, 8-Hydroxyguanosine, and Other C8-Substituted Guanine Nucleosides[1]", *Chem. Res. Toxicol.*, 3, 445-452, (1990).
Egli et al., "Atomic-resolution structure of the cellulose synthase regulator cyclic diguanylic acid", *Proc. Natl. Acad. Sci.*, vol. 87, 3235-3239, (1990).

Gaffney et al., "One-Flask Syntheses of c-di-GMP and the [$R_p,R_p$] and [$R_p,S_p$] Thiophosphate Analogues", *Organic Letters*, vol. 12, No. 14, 3269-3271, (2010).
Garcia-Arriaga et al., "Isostructural Self-Assembly of 2'-Deoxyguanosine Derivatives in Aqueous and Organic Media", *J. Am. Chem. Soc.*, 130, 10492-10493, (2008).
Hyodo et al., "Synthesis of cyclic bis(3'-5')diguanylic acid (c-di-GMP) analogs", *Tetrahedron*, 62, 3089-3094, (2006).
Kline et al., "Design and Synthesis of bis-Carbamate Analogs of Cyclic *bis*-(3'-5')-Diguanylic Acid (c-di-GMP) and the Acyclic Dimer PGPG", *Nucleosides Nucleotides Nucl. Acids*, 27, 1282-1300, (2008).
Liaw et al., "Cyclic diguanylic acid behaves as a host molecule for planar intercalators", *FEBS J.*, vol. 264, No. 2, 223-227, (1990).
Nakayama et al, "Thiazole Orange-Induced c-di-GMP Quadruplex Formation Facilitates a Simple Fluorescent Detection of This Ubiquitous Bioflim Regulating Molecule", *J. Am. Chem. Soc.*, 133, 4856-4864, (2011).
Ross et al., "The Cyclic Diguanylic Acid Regulatory System of Cellulose Synthesis in *Acetobacter xylinum*", *J. Biol. Chem.*, vol. 265, No. 31,18933-18943, (1990).
Smith et al., "Structural and Biochemical Determinants of Ligand Binding by the c-di-GMP Riboswitch", *Biochemistry*, 49, 7351-7359, (2010).
Smith et al., "Structural basis of differential ligand recognition by two classes of bis-(3'-5')-cyclic dimeric guanosine monophosphate-binding riboswitches", *Proc. Natl. Acad. Sci.*, vol. 108, No. 19, 7757-7762, (2011).
Veliath et al., "Synthesis and characterization of C8 analogs of c-di-GMP", *Nucleosides Nucleotides Nucleic Acids*, 30(11), 961-978, (2011).
Wang et al., "Conservative Change to the Phosphate Moiety of Cclic Diguanylic Monophosphate Remarkably Affects Its Polymorphism and Ability to Bind DGC, PDE, and PilZ Proteins", *J. Am. Chem. Soc.*, 133, 9320-9330, (2011).
Witte et al., "Structural Biochemistry of a Bacterial Checkpoint Protein Reveals Diadenylate Cyclase Activity Regulated by DNA Recombination Intermediates", *Mol. Cell*, 30, 167-178, (2008).
Wong et al., "Disodium Guanosine 5'-Monophosphate Self-Associates into Nanoscale Cylinders at pH 8: A Combined Diffusion NMR Spectroscopy and Dynamic Light Scattering Study", *J. Am. Chem. Soc.*, 127, 6990-6998, (2005).
Wu e al., "Helical Structure of Disodium 5'-Guanosine Monophosphate Self-Assembly in Neutral Solution", *J. Am. Chem. Soc.*, 131, 3180-3182, (2009).
Yan et al., "Synthesis and Immunostimulatory properties of the phosphorothioate analogues of cdiGMP", *Biorg. Med. Chem. Lett.*, 18, 5631-5634, (2008).
Zhang et al., "c-di-GMP Displays a Monovalent Metal Ion-Dependent Polymorphism", *J. Am. Chem. Soc.*, 126, 16700-16701, (2004).
Zhang et al., "Polymorphism of the Signaling Molecule c-di-GMP", *J. Am. Chem. Soc.*, 128, 7015-7024, (2006).
Zhao et al., "Thiophosphate Analogs of c-di-GMP: Impact on Polymorphism", *Nucleosides Nucleotides Nucl. Acids*, 28, 352-378, (2009).

\* cited by examiner

*Primary Examiner* — Traviss C McIntosh, III
(74) *Attorney, Agent, or Firm* — Viksnins Harris & Padys PLLP

(57) ABSTRACT

The invention provides analogs cyclic diguanosine monophosphate (c-di-GMP) having different substituents at the guanine C8 position.

19 Claims, 6 Drawing Sheets

BIMOLECULAR        QUARTET

BIMOLECULAR        TETRAMOLECULAR        OCTAMOLECULAR
*anti* (Ba)       all-*syn* (Ts) AND      all-*syn* (Os) AND
                all-*anti* (Ta)         all-*anti* (Oa)

→ FAVORED BY HIGHER CONCENTRATIONS AND BY $K^+$

← FAVORED BY LOWER CONCENTRATIONS AND BY $Li^+$

SYNTHESIS AND CHARACTERIZATION OF C8 ANALOGS OF C-DI-GMP

CROSS-REFERENCE TO RELATED APPLICATION(S)

This patent application claims the benefit of priority of U.S. application Ser. No. 61/372,169, filed Aug. 10, 2010, which application is herein incorporated by reference.

STATEMENT OF GOVERNMENT SUPPORT

This invention was made with government support under Grant # GM 79760 awarded by the National Institutes of Health. The government has certain rights in the invention.

BACKGROUND

The bacterial signaling molecule cyclic diguanosine monophosphate (c-di-GMP) is increasingly recognized as having widespread consequences for human health through its multiple roles. Not only is c-di-GMP a major factor in the activation of bacterial biofilm formation and repression of motility, it also helps to regulate virulence. Further, although c-di-GMP is not a signaling molecule in Eukarya, it has been shown to be an immunostimulatory agent that can trigger the innate immune response in mice. The mechanisms for how c-di-GMP function remain unclear. Accordingly, analogs of c-di-GMP are needed.

SUMMARY OF CERTAIN EMBODIMENTS OF THE INVENTION

Analogs of cyclic diguanosine monophosphate (c-di-GMP) have been synthesized with different substituents at the guanine C8 position. The effects of the substitutions on the metal-dependent polymorphism were evaluated. Of the substitutions, only the $K^+$ salt of c-di-Br-GMP, 2, forms higher order complexes, predominantly two different syn octamolecular complexes. Its $Na^+$ salt, as well as both the $K^+$ and $Na^+$ salts of c-di-thio-GMP, 3, c-di-methylthio-GMP, 4, c-di-phenyl-GMP, 5, and c-di-acetylphenyl-GMP, 6, all form primarily a syn bimolecular structure. These analogs are useful as probes of the biological function of c-di-GMP and as therapeutic agents.

Accordingly, certain embodiments of the invention are directed to a compound of the formula:

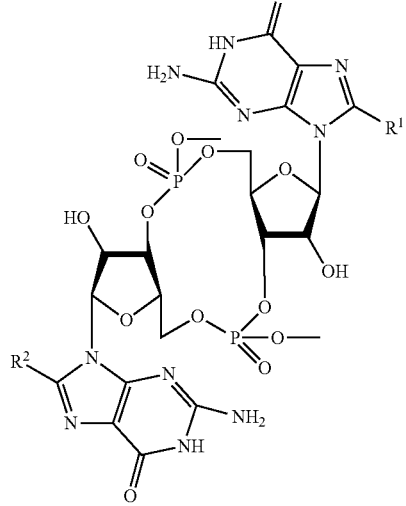

wherein:
$R^1$ an $R^2$ are each independently selected from —$SR_a$, aryl, and halo; and
each $R_a$ is independently H or $(C_1-C_6)$alkyl;
wherein each aryl is optionally substituted with one or more (e.g., 1, 2, 3, or 4) groups independently selected from halo, nitro, cyano, trifluoromethyl, trifluoromethoxy, $(C_1-C_6)$alkoxy, $(C_1-C_6)$alkanoyl, $(C_1-C_6)$alkanoyloxy, $(C_1-C_6)$alkoxycarbonyl, and amino;
or a salt thereof.

In certain embodiments, the compound is

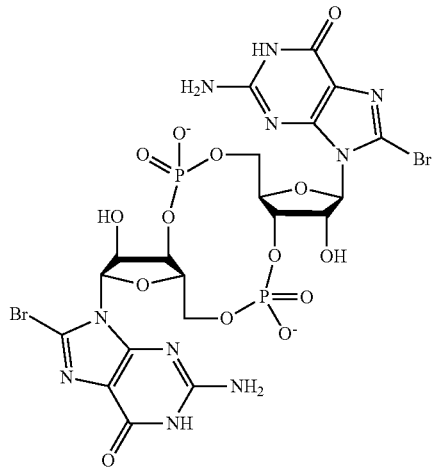

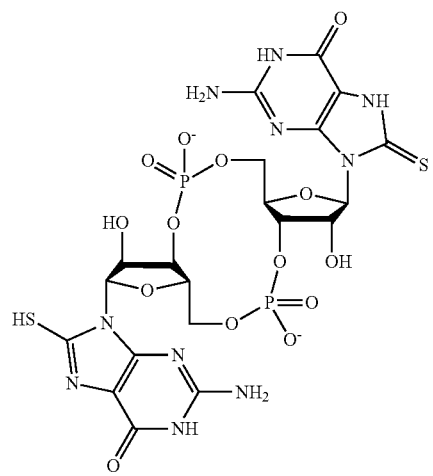

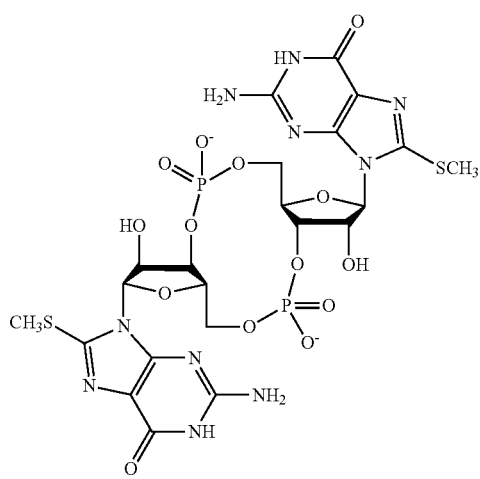

-continued
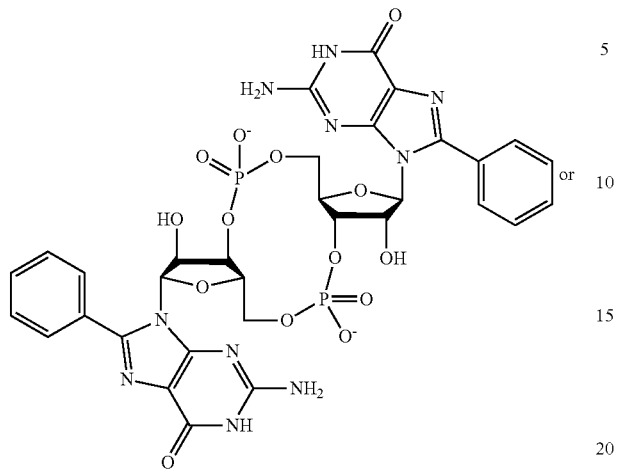
or
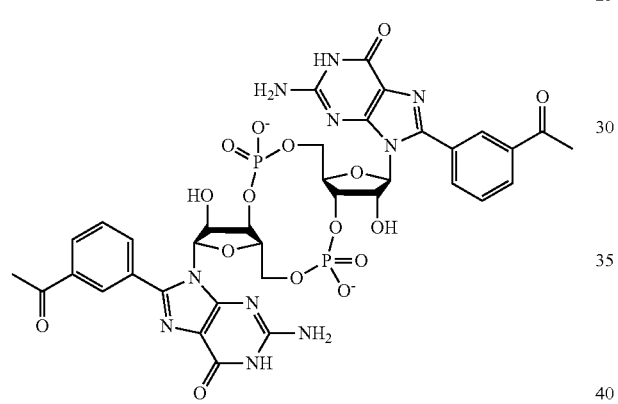
or a salt thereof.
In certain embodiments, the compound is
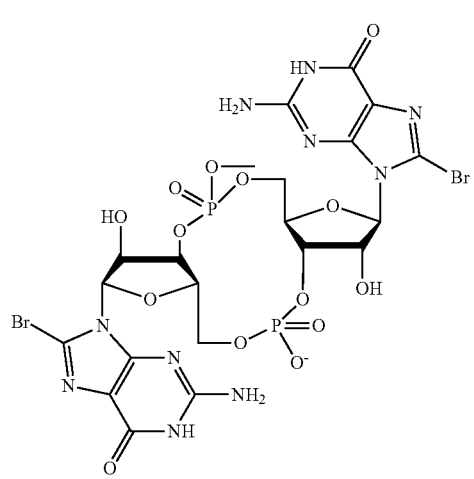
or a salt thereof.
In certain embodiments, the compound is
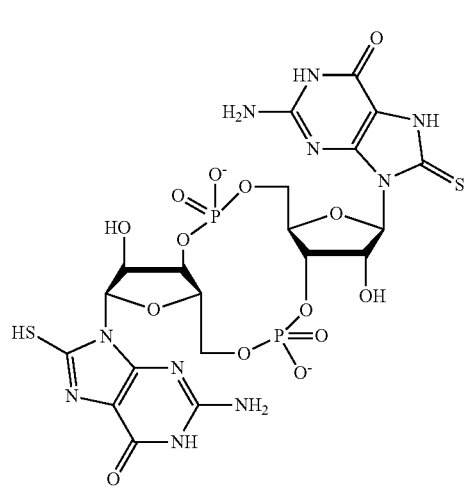
or a salt thereof.
In certain embodiments, the compound is
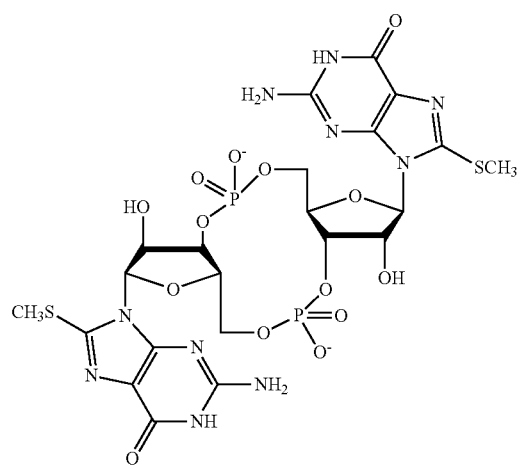
or a salt thereof.
In certain embodiments, the compound is
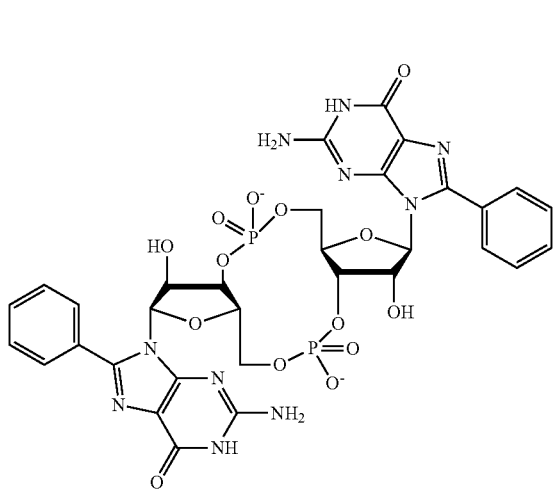
or a salt thereof.

In certain embodiments, the compound is

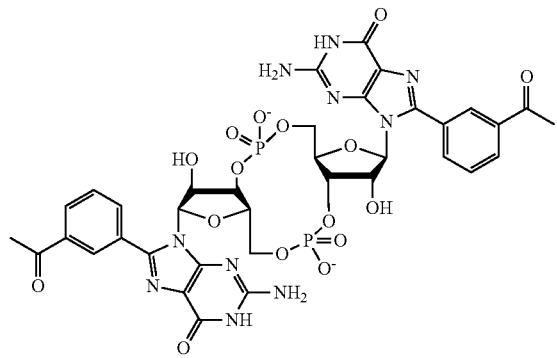

or a salt thereof.

In certain embodiments, the invention is directed to a potassium, sodium or lithium salt of the compound.

In certain embodiments, the invention is directed to a potassium salt of the compound, e.g., of 2.

Certain embodiments of the invention are directed to a composition comprising a compound of the invention, or a salt thereof, and an acceptable carrier.

In certain embodiments, the composition is a pharmaceutical composition that comprises a compound as described herein, or a salt thereof, and a pharmaceutically acceptable carrier.

In certain embodiments, the composition comprises a bimolecular, tetramolecular or octamolecular complex of a compound as described herein, or a salt thereof.

In certain embodiments, the composition comprises a bimolecular complex of a compound as described herein, or a salt thereof.

In certain embodiments, the composition comprises a tetramolecular complex of a compound as described herein, or a salt thereof.

In certain embodiments, the composition comprises an octamolecular complex of a compound as described herein, or a salt thereof.

Certain embodiments of the invention are directed to methods for synthesizing 2, comprising converting 1 to 2.

BRIEF DESCRIPTION OF THE FIGURES

As shown in FIG. 6, c-di-Br-GMP, 2, serves as a key intermediate from which the other analogs are made. The synthesis of 2, 3, 4, 5, and 6 from 1 is shown. Accordingly, certain embodiments of the invention are directed to these synthetic methods of synthesizing 2, 3, 4, 5, and 6.

DETAILED DESCRIPTION

The bacterial signaling molecule cyclic diguanosine monophosphate (c-di-GMP) is a strikingly versatile second messenger that controls the transition between a biofilm-protected sessile state and a single-cell motile state in a wide variety of species. It acts by relaying extracellular signals from the environment to cellular effector receptors that control biofilm formation, expression of virulence factors, organelle formation for motility, cell-cycle differentiation, and a variety of other functions. The effects of c-di-GMP are mediated by its concentration, which is controlled by a balance of its synthesis by diguanylate cyclases and its degradation by specific phosphodiesterases. Further, c-di-GMP can be sequestered at specific sites within the cell, sometimes in a protein-bound form dependent on $K^+$ concentration.

The widespread PilZ family of proteins constitutes the most studied type of c-di-GMP protein receptor, and functions by means of a conformational change upon binding. c-di-GMP has been found to display considerable diversity in its binding modes to PilZ domains, interacting in some cases as a monomolecular unit, and in other cases as a self-intercalated bimolecular structure. In addition, c-di-GMP has a particularly high specific affinity for two different classes of bacterial riboswitch non-coding mRNA domains that help to control transcription and translation by selectively binding small molecules. (Sudarsan et al., Science (Wash.) 2008, 321, 411-413 and Lee et al., Science (Wash.) 2010, 329, 845-848) Crystal structures have shown that in the class I riboswitch, the guanines of c-di-GMP are incorporated into a duplex segment of the aptamer, whereas in the class II riboswitch, they form part of a triplex. However, in spite of these recent advances in knowledge of how c-di-GMP functions, there is not a full understanding of its complex and diverse molecular mechanisms.

Figure 1:
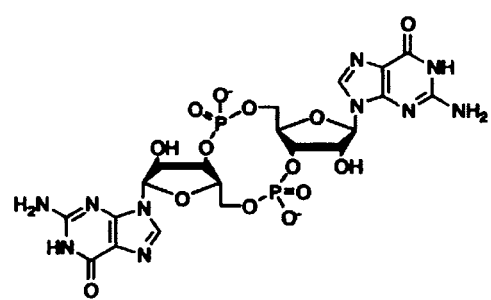
FIG. 1. Structure of c-di-GMP.
Figure 2:
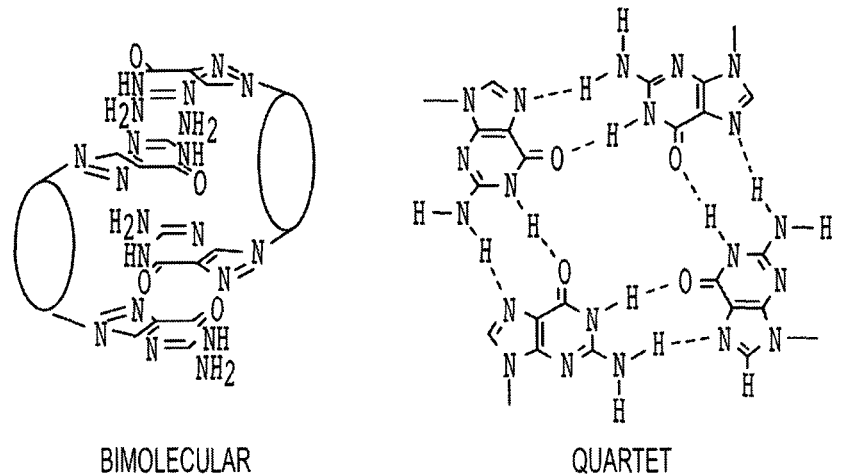
FIG. 2. Cartoons of higher order complexes of c-di-GMP.
Figure 2:
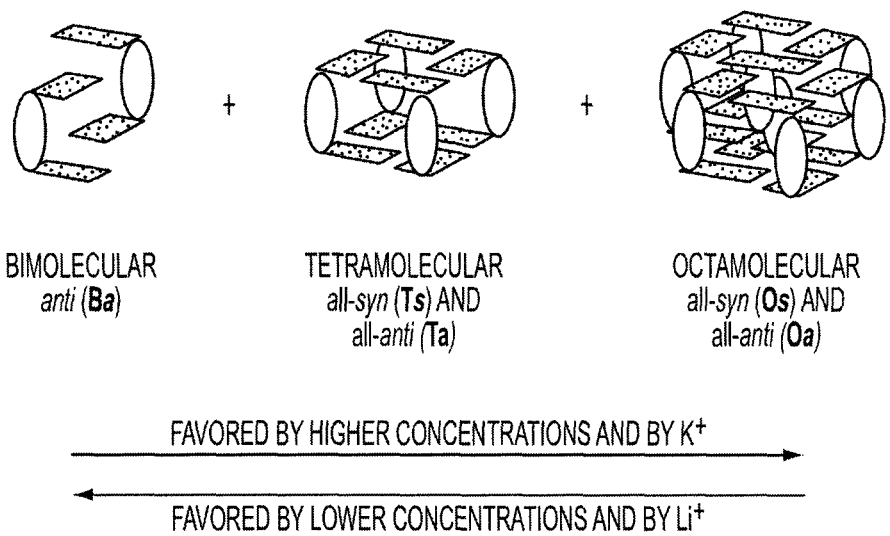

A one-flask gram-scale synthesis for c-di-GMP was recently reported. (Gaffney et al., Org. Lett. 2010, 12, 3269-3271; WO 2011/003025) The c-di-GMP concentration- and metal-dependent polymorphism was investigated, demonstrating that this exceptional molecule can associate to form not only a self-intercalated bimolecular structure, but also tetramolecular and octamolecular guanine quartet complexes (see FIG. 2). A pair of self-intercalated octamolecular quartet complexes dominates the equilibrium of the $K^+$ salt, one with all the guanosines in the anti conformation about the glycosidic bond, and one all syn. The guanosines within these self-intercalated octamolecular complexes are not identical, since eight of them form the 'outer' part of the complex and eight of them are 'inner.' The $Li^+$ and $Na^+$ salts, in contrast, exist as a mixture of the bimolecular, tetramolecular, and octamolecular complexes. NMR and CD work were done with c-di-GMP concentrations higher than physiological conditions. However, the same higher order complexes can form at physiological concentrations when in the presence of certain templating aromatic molecules, along with $K^+$, $Na^+$, or $NH_4^+$. (Nakayama et al., J. Am. Chem. Soc. 2011, 133, 4856-4864) These complexes may therefore be biologically relevant and further study of their properties is of significance.

Synthesis and characterization of c-di-GMP analogs is a useful way to further an understanding of the molecular mechanisms of its complex pathways. Certain analogs were prepared many years ago. (Ross et al., J. Biol. Chem. 1990, 265, 18933-18943) Since then, analogs with several different bases have been reported. (Smith et al., Biochemistry 2010, 49, 7351-7359; Smith et al., Proc. Natl. Acad. Sci. USA 2011, 108, 7757-7762; Amiot et al., Synthesis 2006, 4230-4236; Ching et al., Biorg. Med. Chem. 2010, 18, 6657-6665; Hyodo et al., Tetrahedron 2006, 62, 3089-3094.) One of these, c-di-AMP, has recently been found to be a possible signaling molecule for the detection of chromosomal DNA damage. (Witte et al., Mol. Cell. 2008, 30, 167-178)

The one-flask c-di-GMP route also included synthesis of the [R$_p$,R$_p$] and [R$_p$,S$_p$] dithiophosphate analogs. (Gaffney et al., Org. Lett. 2010, 12, 3269-3271; WO 2011/003025) It was previously shown that the seven diastereomers of the mono-, di-, and trithiophosphates also form higher order guanine quartet complexes. (Zhao et al., Nucleosides Nucleotides Nucl. Acids 2009, 28, 352-378) In particular, the presence of one or two [S$_p$] sulfur atoms specifically stabilizes the anti complexes and/or destabilizes the syn complexes. Others have also reported synthesis of phosphorothioates, although not of the separated diasteromers. (Hyodo et al., Tetrahedron 2006, 62, 3089-3094; Yan et al., Biorg. Med. Chem. Lett. 2008, 18, 5631-5634) A bridging sulfur in the phosphodiester linkage and a backbone-modified analog with bis-carbamate groups in place of the phosphate backbone have been described as well. (Wang et al., J. Am. Chem. Soc. 2011, 133, 9320-9330; Kline et al., Nucleosides Nucleotides Nucl. Acids 2008, 27, 1282-1300).

The syntheses of five c-di-GMP analogs with different substituents at the guanine C8 position, 2-6, is reported herein. These groups introduce a range of steric and electronic alterations, which affect the equilibrium among the possible higher order complexes. These effects have been characterized by UV and NMR, making particular use of 2D DOSY (Diffusion Ordered Spectroscopy) experiments, (Asadi et al., J. Am. Chem. Soc. 2008, 130, 12860-12861; Wong et al., J. Am. Chem. Soc. 2005, 127, 6990-6998; Wu et al., J. Am. Chem. Soc. 2009, 131, 3180-3182) since they had previously provided an exceptionally useful assessment of the size of complexes in earlier work. (Zhang et al., J. Am. Chem. Soc. 2006, 128, 7015-7024; Zhao et al., Nucleosides Nucleotides Nucl. Acids 2009, 28, 352-378)

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, stereoisomeric, or polymorphic form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

Specific values listed below for radicals, substituents, and ranges, are for illustration only; they do not exclude other defined values or other values within defined ranges for the radicals and substituents.

Specifically, (C$_1$-C$_6$)alkyl can be methyl, ethyl, propyl, isopropyl, butyl, iso-butyl, sec-butyl, pentyl, 3-pentyl, or hexyl; (C$_1$-C$_6$)alkoxy can be methoxy, ethoxy, propoxy, iso-propoxy, butoxy, iso-butoxy, sec-butoxy, pentoxy, 3-pentoxy, or hexyloxy; (C$_1$-C$_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; (C$_2$-C$_6$)alkanoyloxy can be acetoxy, propanoyloxy, butanoyloxy, isobutanoyloxy, pentanoyloxy, or hexanoyloxy; and aryl can be phenyl, indenyl, or naphthyl.

The compounds of the invention may exist in one or more tautomeric forms. For example, the compounds may include the tautomers shown below:

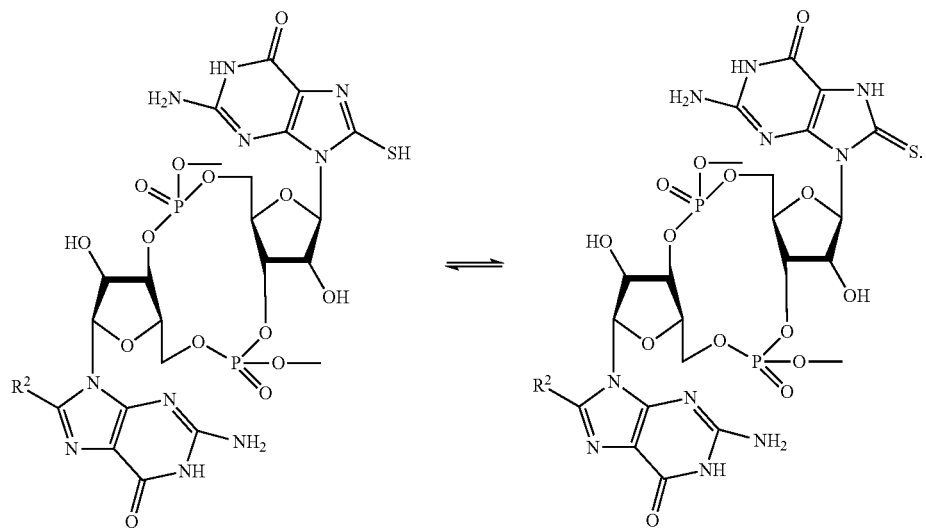

It is to be understood that the present invention encompasses all tautomeric forms of a compound of the invention (e.g., of the analogs 2-6 described herein) as well as mixtures thereof that can exist in equilibrium, which possess the useful properties described herein. The depiction of a single tautomer is understood to represent the compound in all of its tautomeric forms.

Processes for preparing compounds of the invention are provided as further embodiments of the invention and are illustrated by the following procedures in which the meanings of the generic radicals are as given above unless otherwise qualified.

In cases where compounds are sufficiently basic or acidic, a salt of a compound of the invention can be useful, e.g., as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $CF_3SO_3^-$, $p\text{-}CH_3C_6H_4SO_3^-$, citrate, tartrate, malate, fumarate, formate, or acetate.

It will be appreciated by those skilled in the art that a compound of the invention comprising a counterion can be converted to a compound of the invention comprising a different counterion. Such a conversion can be accomplished using a variety of well known techniques and materials including but not limited to ion exchange resins, ion exchange chromatography and selective crystallization.

The compounds of the invention can be formulated as compositions, e.g., pharmaceutical compositions, and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or a salt thereof, required for use in treatment will vary not only with the particular salt selected but also with the route of administration, the nature of the condition being treated and the age and condition of the patient and will be ultimately at the discretion of the attendant physician or clinician.

The compound can be conveniently formulated in unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Certain embodiments of the present invention are directed to capped oligonucleotides (e.g., capped RNA) as described in priority documents U.S. Provisional Application No. 61/372,169, the disclosure of which has been incorporated by reference.

Certain embodiments of the invention will now be illustrated by the following non-limiting Examples.

Example 1

Five analogs of c-di-GMP with different substituents at the guanine C8 position have been synthesized. NMR and UV were used to study their effects on the metal-dependent polymorphism previously demonstrated for the parent compound. Of these, only the $K^+$ salt of c-di-Br-GMP, 2, forms higher order complexes, predominantly two different syn octamolecular ones. Its $Li^+$ and $Na^+$ salts, as well as both the $K^+$ and $Na^+$ salts of c-di-thio-GMP, 3, c-di-methylthio-GMP, 4, c-di-phenyl-GMP, 5, and c-di-acetylphenyl-GMP, 6, all form primarily a syn bimolecular structure, that has a diagnostic amino NMR resonance. These compounds, which favor the syn conformation, complement earlier work with $[S_p]$-phosphorothioate analogs, which favored the anti conformation. (Zhao et al., Nucleosides Nucleotides Nucl. Acids 2009, 28, 352-378)

It is concluded that at UV concentrations (0.320 to 0.039 mM), the $K^+$ and $Na^+$ salts of 2 exist in the monomeric state, because UV melts show no hypochromism. However, at NMR concentrations (26-31 mM), the $Na^+$ and $Li^+$ salts of 2 and the $K^+$ and $Na^+$ salts of 3, 4, 5, and 6 all display evidence of forming primarily the bimolecular structure. In contrast, only the $K^+$ salt of 2 is able to form higher order complexes.

Figure 3:
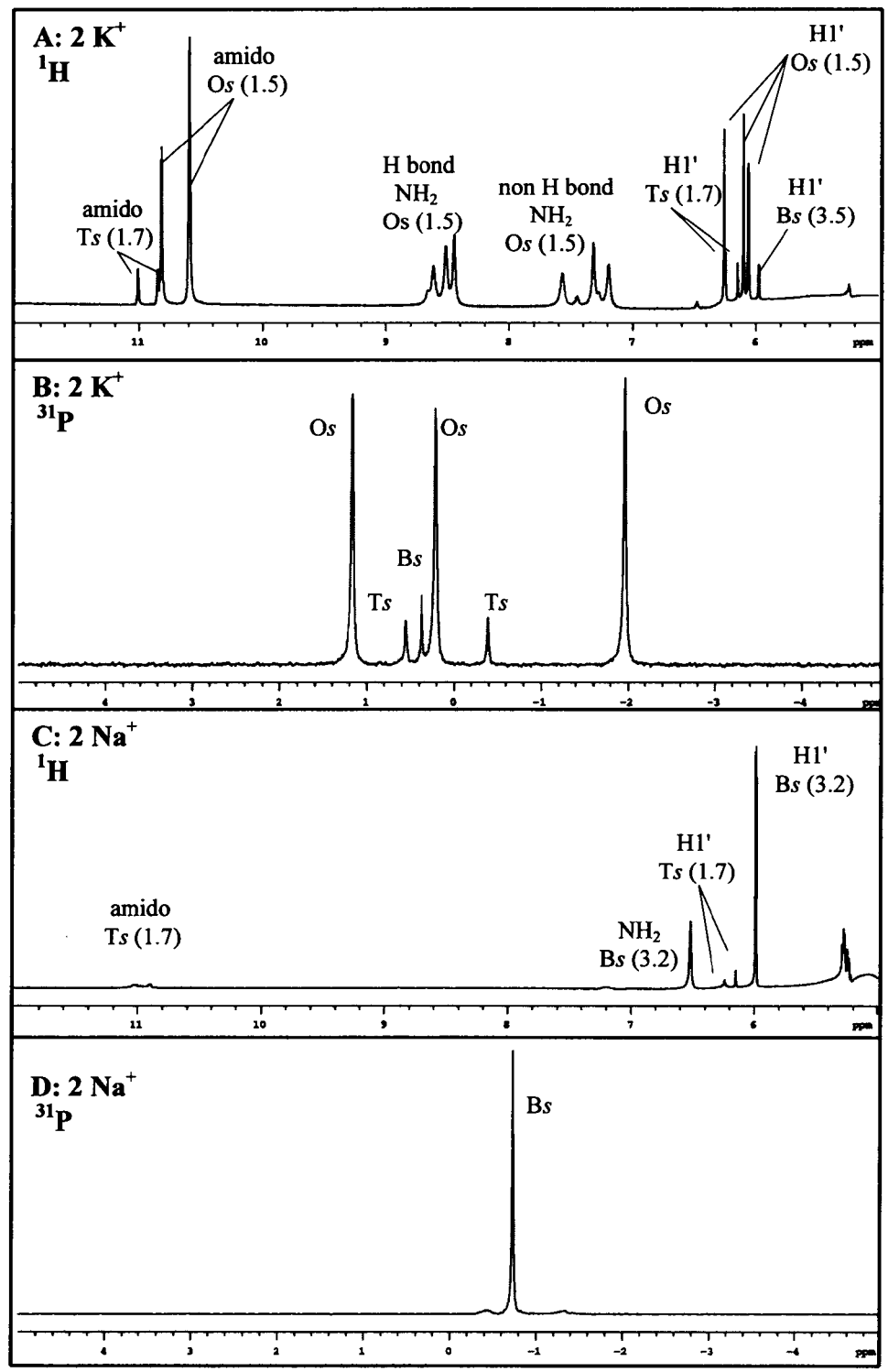
FIG. 3. $^1H$ and $^{31}P$ NMR spectra for $K^+$ and $Na^+$ salts of 2. $^1H$ and $^{31}P$ NMR spectra for $K^+$ and $Na^+$ salts of 2 (Bs=syn bimolecular, Ts=syn tetramolecular, and Os=syn octamolecular, diffusion coefficients in parentheses).

The diffusion constants shown in parentheses in FIG. 3A from the DOSY experiment for the $K^+$ salt of 2 show that it forms predominantly octamolecular complexes, with small amounts of tetramolecular and bimolecular complexes. As expected, the presence of the large bromine atoms in 2 favors the syn conformation about the glycosidic bond, as shown by the 2D HMBC spectrum in FIG. 4A. The 1D $^1$H NMR spectrum in FIG. 3A displays three large H1' resonances, and the $^{31}$P NMR spectrum in FIG. 3B also exhibits three resonances. The syn octamolecular complex can exist in two different forms: one in which the inner and outer guanosines and their phosphates have different enough environments to display different resonances, and another in which they coincide. Similarly, there appear to be two different syn tetramolecular complexes, although in much smaller amounts, leading to two different resonances.

Figure 4:
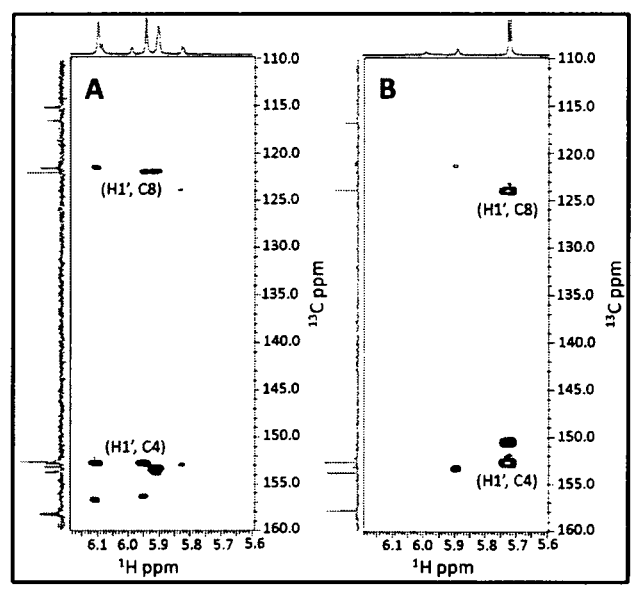
FIG. 4. HMBC spectra. HMBC spectra for A) the $K^+$ salt of 2 at 25° C. and B) the $Na^+$ salt of 2 at 15° C.

The $Na^+$ salt of 2, on the other hand, occurs primarily as the syn bimolecular structure, as seen by the diffusion constants listed in FIG. 3C and the HMBC spectrum in FIG. 4B. The 1D $^1$HNMR spectrum in FIG. 3C displays a single H1' resonance, as well as one amino resonance. The bimolecular form of the parent c-di-GMP occurs in the anti conformation, and does not display any amino resonances protected from exchange. In the crystal structures of c-di-GMP, which show the anti bimolecular structure, the amino groups are positioned towards the outside of the complex, where they can exchange readily with bulk solvent. (Egli et al., Proceedings of the National Academy of Sciences, U.S.A. 1990, 87, 3235-3239; Liaw et al., FEBS J. 1990, 264, 223-227) In the syn bimolecular structure of 2, the aminos presumably are situated closer to the center of the structure, where at least those of the inner guanosines are protected from such exchange. This amino resonance thus appears to be diagnostic for the syn bimolecular structure.

None of the other C8 analogs (3, 4, 5, or 6) displays any evidence for formation of higher order complexes, as seen in FIG. 5A-D. It had been anticipated that the sulfur atoms in c-di-thio-GMP, 3, would exist primarily as the C=S tautomer, perhaps precluding quartet formation because of the presence of the protonated N7. (Cho et al., Chem. Res. Toxicol. 1990, 3, 445-452) The methyl groups in c-di-methylthio-GMP, 4, would prevent such C=S tautomerization, but are somewhat bulky. It had also been considered that the phenyl rings of c-di-phenyl-GMP, 5, could conceivably participate in n-stacking associated with the guanine quartets. Further, the additional acetyl groups on the phenyl rings of c-di-acetylphenyl-GMP, 6, possibly could increase the guanine quartet stability, as has been shown for 2'-deoxyguanosine derivatives in both organic and aqueous solvents. (García-Arriaga et al., J. Am. Chem. Soc. 2008, 130, 10492-10493) However, such stabilization did not occur for 5 and 6. Perhaps the simple presence of bulky groups at the C8 position, with the notable exception of bromine, is sufficient to prevent the cyclic dimer from forming guanine quartet complexes.

Results

Figure 6:
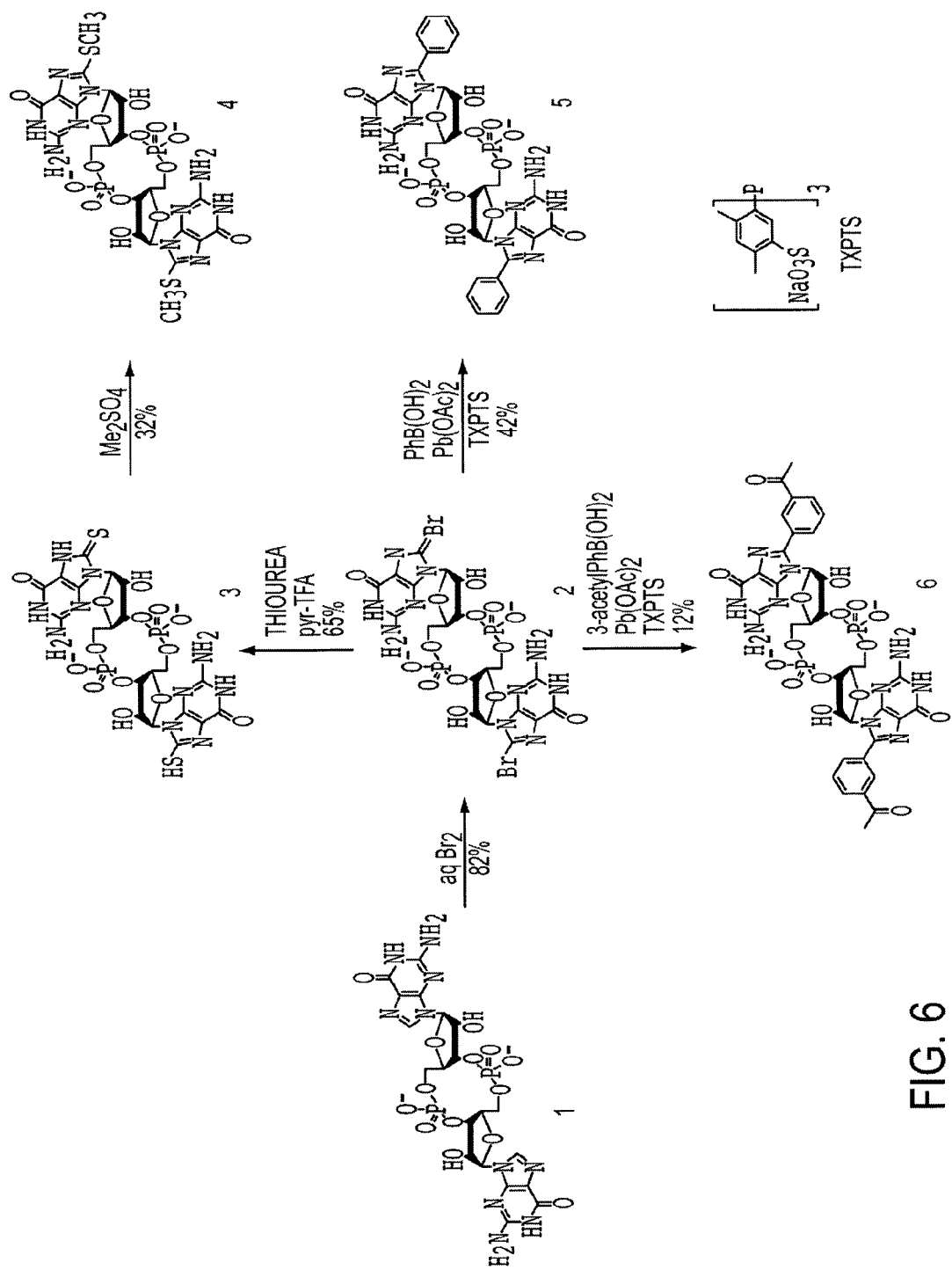
FIG. 6.

As shown in FIG. 6, c-di-Br-GMP, 2, serves as a key intermediate from which the other analogs are made.

Although guanosine can be brominated at the C8 position under a variety of conditions, (Holmes et al., J. Am. Chem. Soc. 1964, 86, 1242-1245; Shapiro et al., Biochem. Biophys. Res. Commun. 1966, 24, 401-405) the current procedure uses aqueous $Br_2$, primarily because of the water solubility of c-di-GMP. A freshly prepared solution of aqueous $Br_2$ (0.24 M, 3.5 equiv) was added to 1 in two portions to form the dibrominated 2. After 2 h, the solution was quenched with cyclohexene, washed with dichloromethane, and concentrated. The product was purified and then desalted by semi-preparative RP HPLC to give 2 as the triethylammonium salt in 82% yield. Portions of 2 were converted to the $K^+$, $Na^+$, and $Li^+$ salts using the corresponding cation exchange resins.

Synthesis of c-di-thio-GMP, 3

Thiourea in refluxing ethanol has been shown to be an effective reagent for thiolation of 8-Br-guanosine. (Holmes et al., J. Am. Chem. Soc. 1964, 86, 1242-1245) However, it was found that reaction of 2 required a more polar solvent system, as well as addition of pyridinium trifluoroactate to catalyze the reaction. Acid alone was not sufficient in promoting the reaction. Presumably, initial protonation of the N7 is followed by displacement of bromine by pyridine, which is in turn replaced by the sulfur from thiourea. Optimized conditions entailed heating 2 at 60° C. in 30% aqueous ethanol with 4 equiv of thiourea and 0.4 equiv of pyridinium trifluoroacetate for 22 h. The solution was concentrated, and the product purified and then desalted by semi-preparative RP HPLC to give 3 as the triethylammonium salt in 65% yield. Portions of 3 were converted to the $K^+$ and $Na^+$ salts using the corresponding cation exchange resins.

Synthesis of c-di-methylthio-GMP, 4

Methylation of 3 to give 4 was accomplished readily using 4.5 equiv of dimethylsulfate in dry DMF for 4 h. (Holmes et al., J. Am. Chem. Soc. 1964, 86, 1242-1245) Some incomplete reaction as well as over-methylation at other sites were unavoidable, but were minimized by these conditions. The solution was diluted with an aqueous buffer, washed with ether, and concentrated. The product was purified and then desalted by semi-preparative RP HPLC to give 4 as the triethylammonium salt in 32% yield. Portions of 4 were converted to the $K^+$ and $Na^+$ salts using the corresponding cation exchange resins.

Synthesis of c-di-phenyl-GMP, 5

Arylation of 8-Br-G has been reported using a convenient palladium-catalyzed Suzuki coupling reaction. (Western et al., J. Org. Chem. 2003, 68, 6767-6774) It is regiospecific for the C8 and can be carried out in an aqueous solution. Similar conditions were used, with 3.2 equiv of phenylboronic acid, 0.08 equiv of palladium acetate, 0.24 equiv of the water-soluble phosphine ligand tris(4,6-dimethyl-3-sulfonatophenyl)phosphine (TXPTS), and 3 equiv of $Na_2CO_3$ in water heated to 95° C. for 20 h. Although the coupling was successful, the high temperature and pH partially hydrolyzed the phosphodiester backbone of the product. The solution was neutralized, washed with ethyl acetate, and concentrated. The palladium catalyst was removed on a RP pre-column, and the product was purified and then desalted by semi-preparative RP HPLC to give 5 as the triethylammonium salt in 42% yield. Portions of 5 were converted to the $K^+$ and $Na^+$ salts using the corresponding cation exchange resins.

Synthesis of c-di-acetylphenyl-GMP, 6

Conditions used to prepare 5 were adapted for 6, using 3-acetylphenyl boronic acid, and a lower temperature of 80° C. to avoid excessive hydrolysis. After concentration and removal of the palladium catalyst, the product partially crystallized from a 1:1 $H_2O:CH_3OH$ solution as the $CH_3OH$ was slowly removed, giving 6 as the triethylammonium salt in 12% yield. Portions of 6 were converted to the $K^+$ and $Na^+$ salts using the corresponding cation exchange resins.

UV Melting of c-di-Br-GMP, 2

The UV absorbance of samples of the $K^+$ and $Na^+$ salts of 2 at concentrations ranging from 0.320 to 0.039 mM was monitored as a function of increasing temperature. No hypochromic effects were observed, indicating an absence of stacking that is associated with bimolecular and higher order complexes. In contrast, the parent compound showed pronounced hypochromism at similar concentrations. (Zhang et al., J. Am. Chem. Soc. 2004, 126, 16700-16701)

NMR of $K^+$ salt of c-di-Br-GMP, 2

A portion of the $^1H$ NMR spectrum of the $K^+$ salt of 2 at 25° C. is shown in FIG. 3A. Three larger and three smaller resonances clustered near 6 ppm, from the H1' were observed. Diffusion coefficients (D, $m^2/s \times 10^{-1}$), obtained from a separate 2D DOSY experiment on the same sample, are indicated in parentheses. In earlier work on polymorphism of the parent c-di-GMP and the thiophosphate analogs,[23] we found that at 30° C., octamolecular complexes had diffusion coefficients in the range 1.5-1.9, tetramolecular complexes 1.7-2.4, and the bimolecular structure 3.2-3.9. (Zhang et al., J. Am. Chem. Soc. 2006, 128, 7015-7024; Zhao et al., Nucleosides Nucleotides Nucl. Acids 2009, 28, 352-378) Here, all three larger resonances have D=1.5, indicative of octamolecular complexes. The two farthest downfield of the three smaller resonances have D=1.7, indicative of tetramolecular complexes (the octamolecular having been already identified), and the remaining farthest upfield smaller resonance has D=3.5, indicative of a bimolecular structure. At 5° C., all three smaller resonances nearly disappear, leaving primarily the three larger ones. The octamolecular complexes are expected to be preferentially stabilized at lower temperatures. At 55° C., the three larger resonances all decrease, and only the farthest upfield of the smaller resonances increases, confirming it is the bimolecular structure. The higher order complexes are disrupted at higher temperatures, leaving the bimolecular structure dominant.

FIG. 3A also shows resonances typical of guanine quartet structures for non-H bonded amino groups from 7.1-7.6 ppm (D=1.5), for H bonded amino groups from 8.4-8.7 ppm (D=1.5), and for N1 amido groups from 10.5-11 ppm (D=1.5 and 1.7). These are consistent with the tetra- and octamolecular complexes, in which they are protected from exchange. All these resonances increase at 5° C. and decrease at 55° C.

Because these analogs lack H8 atoms, 2D NOESY experiments were not used to make syn and anti assignments. 2D heteronuclear experiments were used, described below.

The $^{31}P$ NMR spectrum of the $K^+$ salt of 2 at 25° C. is shown in FIG. 3B. The three larger resonances increase at 5° C. and decrease at 55° C., consistent with the octamolecular complexes seen in the $^1H$ NMR. Of the three smaller resonances, only the central one increases significantly at 55° C., demonstrating that it represents the bimolecular structure.

NMR of $Na^+$ salt of c-di-Br-GMP, 2

A portion of the $^1H$ NMR spectrum of the $Na^+$ salt of 2 at 25° C. is shown in FIG. 3C. In the H1' region around 6 ppm, a single large resonance dominates (D=3.2). Only traces of H1' and N1 amido resonances with D=1.7 appear. However, a resonance of medium intensity is present at 6.5 ppm (D=3.2), consistent with an amino group that is protected from exchange in the bimolecular structure. This resonance becomes larger at 5° C. and disappears completely at 55° C. A sample of the $Na^+$ salt of the monomer 8-Br-GMP at the same conditions does not exhibit this amino resonance.

The $^{31}P$ NMR spectrum of the $Na^+$ salt of 2 at 25° C., shown in FIG. 3D, displays primarily a single resonance, with two small resonances appearing on each side of it at 5° C. These $^1H$ and $^{31}P$ NMR results demonstrate the much lower stability of higher order complexes of the $Na^+$ salt of 2, relative to the $K^+$ salt.

NMR of $Li^+$ salt of c-di-Br-GMP, 2

The $^1H$ NMR spectrum of the $Li^+$ salt of 2 shows only a single resonance for the HP and one resonance for the amino, even at 5° C. Correspondingly, the $^{31}P$ NMR spectrum also shows only a single resonance. The spectra are very similar to those of the $Na^+$ salt of 2. $Li^+$ does not enhance guanine quartet formation, so it was not surprising that only the bimolecular structure is present for the $Li^+$ salt of 2.

HMBC 2D NMR of $K^+$ and $Na^+$ salts of c-di-Br-GMP, 2

A $^1H$-$^{13}C$ Heteronuclear Multiple Bond Correlation (HMBC) spectrum of the $K^+$ salt of 2 at 25° C. is shown in FIG. 4A. Because the H1'-C4 crosspeaks are somewhat stronger than the H1'-C8 crosspeaks for all three of the larger HP resonances, it was concluded that they all represent octamolecular complexes with a syn conformation around the glycosidic bond. The bulky bromine at C8 is expected to favor the syn conformer, so it was not surprising that no evidence for complexes with the anti conformation was demonstrated.

A HMBC spectrum of the Na$^+$ salt of 2 at 15° C. is shown in FIG. 4B. At this lower temperature, the resonances have shifted upfield by 0.35 ppm. Here, the H1'-C4 and H1'-C8 crosspeaks for the bimolecular structure are of similar intensities. In contrast, similar analysis of the bimolecular structure of the Li$^+$ salt of the parent c-di-GMP shows a clear H1'-C8 cross-peak with no visible H1'-C4 crosspeak, indicative of the anti conformation. (Zhang et al., J. Am. Chem. Soc. 2006, 128, 7015-7024) Thus, the comparable H1'-C4 and H1'-C8 crosspeaks for the bimolecular structure of the Na$^+$ salt of 2 support its syn conformation. Further, crosspeaks for the small resonance at 5.9 ppm for one of the two tetramolecular complexes also indicate a syn conformation. In addition, the $^1$H resonance at 6.5 ppm was assigned in FIG. 3C to an amino group that is protected from exchange. The lack of any crosspeaks for this $^1$H resonance to a carbon in FIG. 4B confirms this assignment.

NMR of K$^+$ and Na$^+$ salts of c-di-thio-GMP, 3

Figure 5:
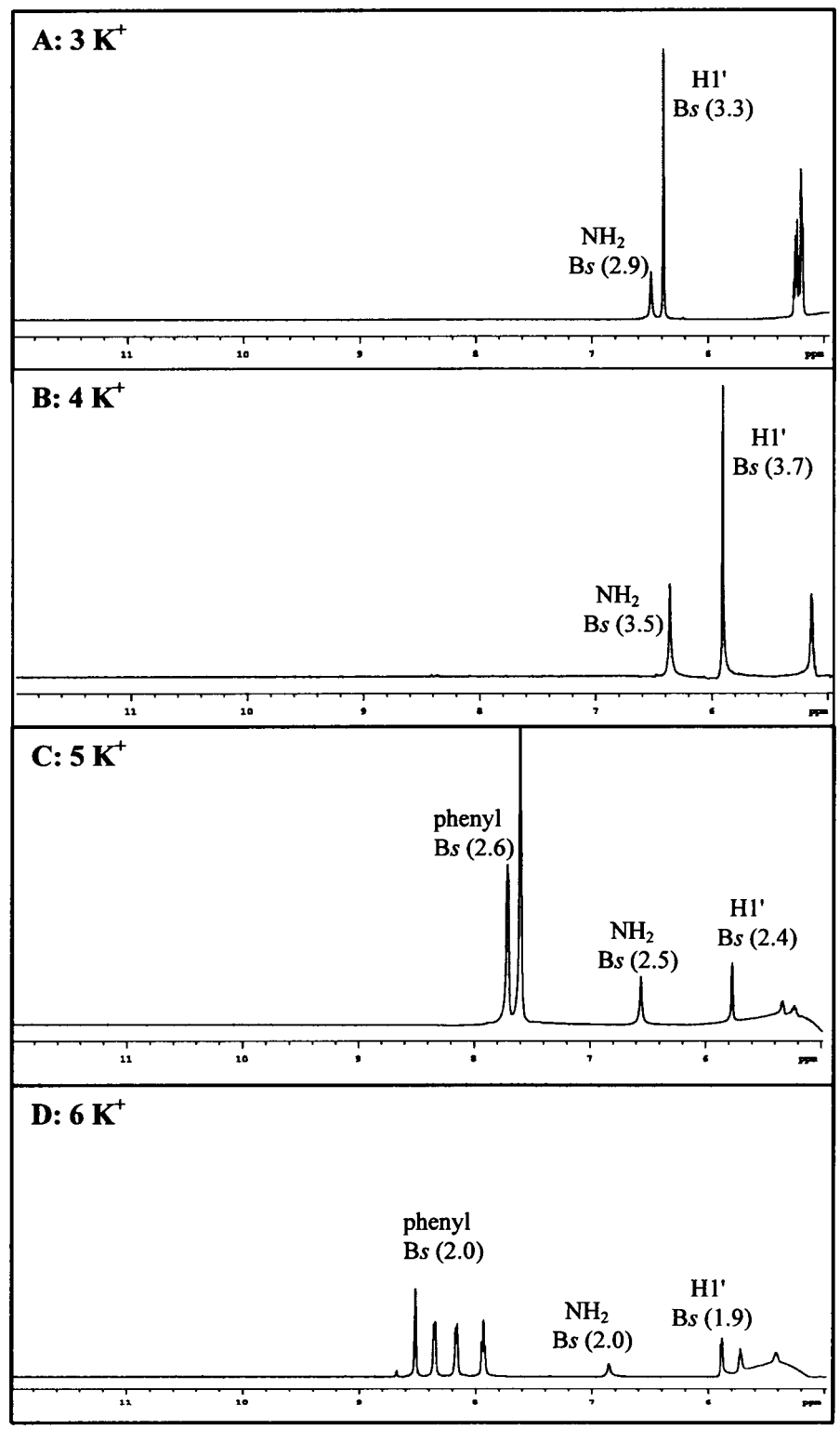
FIG. 5. $^1H$ NMR spectra for $K^+$ salts of 3, 4, 5, and 6 (Bs=syn bimolecular, diffusion coefficients in parentheses).

A portion of the $^1$H NMR spectrum of the K$^+$ salt of 3 at 25° C. is shown in FIG. 5A. No resonances that are characteristic of guanine quartet structures were observed. There is a single H1' resonance (D=3.3), consistent with the bimolecular structure. Like the Na salt of 2, in which the syn bimolecular structure dominates, a small resonance at 6.5 ppm (D=2.9) is also present, consistent with an amino group that is protected from exchange in the bimolecular structure. Again, this resonance becomes larger at 5° C. and disappears completely at 55° C. The $^{31}$P NMR spectrum shows only a sharp singlet, supporting this conclusion. The $^1$H and $^{31}$P NMR spectra of the Na$^+$ salt of 3 are very similar to those of its K$^+$ salt.

NMR of c-di-methylthio-GMP, 4, c-di-phenyl-GMP, 5, and c-di-acetylphenyl-GMP, 6

Portions of the $^1$H NMR spectra of the K$^+$ salts of 4, 5, and 6 at 25° C. are shown in FIGS. 5B, 5C, and 5D, respectively. Because 6 was not soluble in water, its spectra were obtained in 1:1 CH$_3$OD:H$_2$O. As seen for 3, no resonances characteristic of guanine quartet structures were observed, single H1' resonances around 6 ppm and amino resonances slightly farther downfield are demonstrated, in addition to resonances from the C8 substituents. For 4, 5, and 6, the H1'/amino resonances display nearly identical diffusion constants of 3.7/3.5, 2.4/2.5, and 1.9/2.0, respectively. These resonances become larger at 5° C. and disappear completely at 55° C. In all three cases, $^1$H spectra of the Na$^+$ salts closely resemble those of the K$^+$ salts.

General Methods

Semi-preparative RP HPLC purification was performed on a Waters Novapak C18 19×300 mm column using gradients of acetonitrile and 0.1M aq triethylammonium acetate (TEAA) (pH 6.8). Desalting of purified samples was performed on a Waters Novapak C18 19×300 mm column using gradients of acetonitrile and degassed Millipore water. Analytical RP HPLC was performed on a Waters 2960 system, with an Atlantis C18 column, 100 Å, 4.6 mm×50 mm, 3 µm using gradients of acetonitrile and 0.1M aq TEAA (pH 6.8) at a flow rate of 1.0 mL/min. ESI-MS was acquired using a Waters Micromass single quadrupole LCZ system. K$^+$, Na$^+$, and Li$^+$ salts were obtained by cation exchange using 15 mL of AG 50W-X2 sulfonic acid resin, which had been converted to their corresponding forms. Maximum UV absorbance for all analogs was determined in TEAA buffer (pH 6.8) at 25° C. and 75° C. on an Aviv 14DS UV/VIS spectrophotometer. The extinction coefficients of the analogs were determined by dissolving a known mass of a lyophilized sample in 10 mM sodium citrate-phosphate buffer (pH 6.8), after having Karl Fischer analysis done for determination of water content. Absorbances of the samples and blanks were measured in a 1 cm path length quartz cell at 25° C. in triplicate. The average value was used to calculate the extinction coefficient based on Beer's Law, $\epsilon$=A/lc.

UV Melting Experiments

Stock solutions of the K$^+$ and Na$^+$ salts of 2 were prepared in 0.1 M KCl or NaCl, and 10 mM K$^+$ or Na$^+$ citrate-phosphate buffer at pH 6.8, as appropriate. A series of dilutions was made to give four final concentrations between 0.320 and 0.039 mM. The samples were placed in different path length quartz cells, and UV absorbance was monitored as a function of temperature from 4° C. to 80° C. at 263 nm.

NMR

All NMR spectra were acquired on a Varian VNMRS 500 MHz spectrometer. Samples were 31 mM of 2, 27 mM of 3, 26 mM of 4, 28 mL of 5, and 26 mM of 6, each in 0.30 mL H$_2$O containing 10% D$_2$O. The pH of all samples was adjusted to 6.8, using either HCl or KOH/NaOH/LiOH, as appropriate. Each sample was heated to 75° C. for 10 minutes, then allowed to cool to room temperature before being transferred to the NMR tube. The $^1$H and $^{13}$C NMR spectra were referenced to sodium trimethylsilylpropylsulfonate in D$_2$O, and the $^{31}$P NMR spectra were referenced to 10% phosphoric acid in D$_2$O. The 1D $^1$H NMR spectra used frequency pre-saturation for water suppression. The DOSY spectra used a pre-saturation pulse for water suppression. The data were collected using a 2.5 second relaxation delay over an 8000 Hz spectral width, with 16 repetitions over 256 increments and a diffusion delay of 0.1 seconds. For the HMBC experiments, the $^1$H spectra were acquired with 16 scans, with acquisition time and relaxation delay of 2 s and 1.5 s, respectively. To suppress water, $^1$H pre-saturation was applied during the relaxation delay. The $^{13}$C spectra were acquired with 1024 scans, with acquisition time and relaxation delay of 0.5 s and 1 s, respectively. For NOE enhancement and $^1$H decoupling, $^1$H WALTZ16 decoupling was applied during the entire experiment. $^1$H-$^{13}$C HMBC 2D spectra were acquired using 2048 (t2) times 100 (t1) complex points with spectral widths of 8000 Hz (t2) and 10000 Hz (t1) and transformed to spectra with 2048 (D1) times 1024 (D2) real points after two times linear prediction in t1. The number of scans per each t1 increment was 128 and the relaxation delay for each scan was 1.5 s. To suppress water, $^1$H pre-saturation was applied during the relaxation delay. The DEPT transfer delay for HMBC was chosen as $^{2,3}$J$_{HC}$=20 Hz (the multi-bond coupling constant) and $^1$J$_{HC}$ (the one-bond coupling constant) was set as 140 Hz to suppress cross peaks contributed from the one-bond $^1$H-$^{13}$C connectivity.

Synthesis of cyclo-8-bromoguanosinylyl (3'→5')-8'-bromoguanosinylyl (3'→5'), triethylammonium salt (c-di-Br-GMP, 2). To a stirred solution of 1 (0.19 g, 0.22 mmol, TEA$^+$ salt) in 2 mL of water, was added a freshly prepared solution of 0.24 M aqueous bromine (2.7 mL, 0.65 mmol, 3.0 equiv). After 1 h, additional aqueous bromine was added (0.5 mL, 0.11 mmol, 0.50 equiv). After 1 additional h, 3 mL of cyclohexene was added and the mixture was stirred vigorously. The mixture was diluted with 8 mL of water, and then washed with three 5 mL portions of dichloromethane. The aqueous layer was concentrated on a speedvac to remove traces of organic solvent, and then lyophilized. The product was purified by semi-preparative RP HPLC and then desalted to give 0.19 g of 2 (0.18 mmol, 82%) in the triethylammonium form. UV $\lambda_{max}$ (25° C.) 263 nm; ε (25° C., pH 6.8) 32,800 OD M$^{-1}$cm$^{-1}$; $^1$H NMR: δ 6.46 (br s), 5.90 (d, J=3.5 Hz, 2H), 5.21-5.15 (m, water suppression reduces intensity), 4.26-4.23 (m, water suppression reduces intensity), 4.10-4.07 (m, 2H), 3.11 (q, J=7.5 Hz, 12H), 1.19 (t, J=7.5 Hz, 18H); $^{13}$C NMR: δ 160.1, 156.3, 155.2, 126.4, 119.3, 93.3, 82.8 (app t, J$_{CP}$=8.6 Hz), 74.1 (d, J$_{CP}$=5.0 Hz), 73.4, 65.1 (J$_{CP}$=5.0 Hz), 49.3, 10.9; $^{31}$P NMR: δ−0.83 (s). The mass was confirmed by ESI-MS in negative mode as m/z (M−1) 847.4 (calculated for C$_{20}$H$_{21}$Br$_2$N$_{10}$O$_{14}$P$_2^-$: 847.2).

Synthesis of cyclo-8-thioguanosinylyl (3'→5')-8'-thioguanosinylyl (3'→5'), triethylammonium salt (c-di-thio-GMP, 3). To 2 (0.180 g, 0.17 mmol, TEA$^+$ salt), thiourea (0.052 g, 0.68 mmol, 4.0 equiv), and pyridinium trifluoroacetate (0.013 g, 0.68 mmol, 0.4 equiv) were added 2.5 mL of degassed water and 1.0 mL of degassed ethanol under a nitrogen atmosphere. The mixture was heated in a 60° C. oil bath for 22 h. The cooled reaction mixture was diluted with 3 mL of water and lyophilized. The product was purified by semi-preparative RP HPLC, and desalted to give 0.105 g of 3 (0.110 mmol, 65%) as the triethylammonium salt. UV λ$_{max}$ (25° C.) 302, 286 (shoulder) nm; ε (25° C., pH 6.8) 38,200 OD M$^{-1}$cm$^{-1}$; $^1$H NMR: δ 6.49 (br s), 6.37 (d, J=2.5 Hz, 2H), 5.24-5.15 (m, water suppression reduces intensity), 4.27-4.21 (m, water suppression reduces intensity), 4.10-4.07 (m, 2H), 3.11 (q, J=7.5 Hz, 12H), 1.20 (t, J=7.5 Hz, 18H); $^{13}$C NMR: δ 167.6, 156.6, 155.2, 153.0, 107.2, 92.4, 82.3 (app t, J$_{CP}$=9.5 Hz), 74.2 (d, J$_{CP}$=4.0 Hz), 65.1 (d, J$_{CP}$=4.0 Hz), 49.3, 10.9; $^{31}$P NMR: δ−0.78 (s). The mass was confirmed by ESI-MS in negative mode as m/z (M−1) 753.4 (calculated for C$_{20}$H$_{23}$N$_{10}$O$_{14}$P$_2$S$_2^-$: 753.5).

Synthesis of cyclo-8-methylthioguanosinylyl (3'→5')-8'-methylthioguanosinylyl (3'→5'), triethylammonium salt (c-di-methylthio-GMP, 4). To 3 (0.089 g, 0.093 mmol, TEA$^+$ salt) was added 1.0 mL of dry DMF. The mixture was dried by evaporation of acetonitrile and placed under a nitrogen atmosphere. A solution of 0.7 M dimethylsulfate in dry DMF (0.60 mL, 0.42 mmol, 4.5 equiv) was added and allowed to react 4 hours. The reaction was quenched with 1 mL of aqueous MeOH, diluted with 5 mL of 0.1M TEAA buffer (pH 6.8), and washed with three 5 mL portions of ethyl ether. The aqueous layer was concentrated on a speedvac to remove traces of organic solvent, and lyophilized. The product was purified by semi-preparative RP HPLC, and desalted to give 0.030 g of 4 (0.029 mmol, 32%) as the triethylammonium salt. UV λ$_{max}$ (25° C.) 274 nm; ε (25° C., pH 6.8) 41,100 OD M$^{-1}$cm$^{-1}$; $^1$H NMR: δ 5.89 (d, J=4.0 Hz, 2H), 5.13-5.10 (m, water suppression reduces intensity), 4.25-4.23 (m, water suppression reduces intensity), 4.10-4.08 (m, 2H), 3.11 (q, J=7.5 Hz, 12H), 2.59 (s, 6H), 1.20 (t, J=7.5 Hz, 18H); $^{13}$C NMR: δ 160.4, 156.1, 155.8, 150.6, 119.2, 91.9, 82.8 (app t, J$_{CP}$=9.0 Hz), 74.3 (d, J$_{CP}$=5.0 Hz), 73.7, 65.1 (d, J$_{CP}$=5.0 Hz), 49.4, 18.0, 10.9; $^{31}$P NMR: δ−0.73 (s). The mass was confirmed by ESI-MS in negative mode as m/z (M−1) 781.5 (calculated for C$_{22}$H$_{27}$H$_{10}$O$_{14}$P$_2$S$_2^-$: 781.6).

Synthesis of cyclo-8-phenylguanosinylyl (3'→5')-8'-phenylguanosinylyl (3'→5'), triethylammonium salt (c-di-Ph-GMP, 5). To 2 (0.12 g, 0.19 mmol, TEA$^+$ salt), phenylboronic acid (0.046 g, 0.38 mmol, 3.2 equiv), palladium acetate (0.002 g, 0.0094 mmol, 0.08 equiv), tris(4,6-dimethyl-3-sulfonatophenyl)phosphine (0.019 g, 0.028 mmol, 0.24 equiv), and sodium carbonate (0.038 g, 0.35 mmol, 3 equiv) was added 2 mL of freshly degassed water under a nitrogen atmosphere. The mixture was heated in a 95° C. oil-bath for 20 h. The cooled reaction mixture was neutralized with 1 M HCl, and then washed with three 5 mL portions of ethyl acetate. The aqueous layer was concentrated on a speedvac to remove traces of organic solvent and lyophilized. A Waters PoraPak 20 cc reverse-phase pre-column was used to separate the palladium catalyst. Further purification was done by semi-preparative RP HPLC, followed by desalting to give 0.052 g of 5 (0.050 mmol, 42%) as the triethylammonium salt. UV λ$_{max}$ (25° C.) 280 nm; ε (25° C., pH 6.8) 43,800 OD M$^{-1}$cm$^{-1}$; $^1$H NMR: δ 7.66-7.65 (m, 4H), 7.55-7.54 (m, 6H), 6.51 (br s), 5.70 (d, J=4.0 Hz, 2H), 5.30-5.28 (m, water suppression reduces intensity) 5.17-5.12 (m, water suppression reduces intensity), 4.31-4.29 (m, water suppression reduces intensity), 4.16-4.11 (m, 2H), 3.07 (q, J=7.5 Hz, 12H), 1.16 (t, J=7.5 Hz, 18H); $^{13}$C NMR: δ 161.0, 156.2, 155.0, 152.6, 133.3, 132.0, 131.6, 130.4, 118.6, 92.9, 82.3 (app t, J$_{CP}$=10.0 Hz), 73.7, 73.0, 65.1, 49.3, 10.9; $^{31}$P NMR: δ−0.77 (s). The mass was confirmed by ESI-MS in negative mode as m/z (M−1) 841.5 (calculated for C$_{32}$H$_{31}$N$_{10}$O$_{14}$P$_2^-$: 841.6).

Synthesis of cyclo-8-(3-acetylphenyl)-guanosinylyl (3'→5')-8'-(3-acetylphenyl)-guanosinylyl(3'→5'), triethylammonium salt (c-di-acetylphenyl-GMP, 6). To 2 (0.91 g, 0.087 mmol, TEA$^+$ salt), 3-acetylphenylboronic acid (0.046 g, 0.28 mmol, 3.2 equiv), palladium acetate (0.002 g, 0.007 mmol, 0.08 equiv), tris(4,6-dimethyl-3-sulfonatophenyl) phosphine (0.014 g, 0.021 mmol, 0.24 equiv), and sodium carbonate (0.028 g, 0.26 mmol, 3.0 equiv) was added 2 mL of freshly degassed water under a nitrogen atmosphere. The mixture was heated in a 80° C. oil-bath for 20 h. The cooled reaction mixture was neutralized with 1 M HCl, and then washed with three 5 mL portions of ethyl acetate. The aqueous layer was concentrated on a speedvac to remove traces of organic solvent and lyophilized. The crude solid was dissolved in 15 mL of 50% aqueous MeOH, filtered through a 0.45 μm filter, and then placed on a speedvac to remove MeOH to induce crystallization. After the supernatant was decanted, the product was isolated as a white solid pellet to give 0.012 g of 6 (0.011 mmol, 12%) as the triethylammonium salt. UV λ$_{max}$ (25° C.) 281 nm; ε (25° C., pH 6.8) 36,500 OD M$^{-1}$cm$^{-1}$; $^1$H NMR: δ 8.25 (s, 2H), 8.08 (d, J=7.0 Hz, 2H), 7.96 (d, J=8.0 Hz, 2H), 7.70 (app t, J=7.5 Hz, 2H), 6.50 (br s), 5.70 (d, J=4.0 Hz, 2H), 5.33-5.31 (m, water suppression reduces intensity) 5.21-5.18 (m, water suppression reduces intensity), 4.33-4.31 (m, water suppression reduces intensity), 4.17-4.12 (m, water suppression reduces intensity), 3.10 (q, J=7.5 Hz, 12H), 2.70 (s, 6H), 1.19 (t, J=7.5 Hz, 18H); $^{13}$C NMR: δ 204.2, 161.4, 156.5, 155.8, 151.6, 140.0, 137.2, 132.8, 132.5, 132.4, 131.9, 119.3, 92.8, 83.8, 75.9, 73.4, 65.8 49.5, 29.0, 11.0; $^{31}$P NMR: δ−0.90 (s). The mass was confirmed by ESI-MS in negative mode as m/z (M−1) 925.7 (calculated for C$_{36}$H$_{35}$N$_{10}$O$_{16}$P$_2^-$: 925.7).

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A compound of the formula:

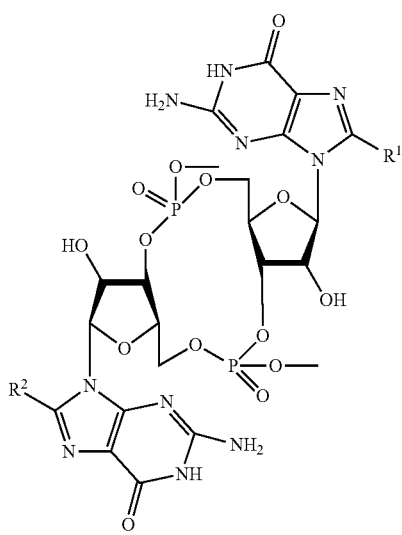

wherein:
R$^1$ and R$^2$ are each independently selected from —SR$_a$, aryl, and halo; and
each R$_a$ is independently H or (C$_1$-C$_6$)alkyl;
wherein each aryl is optionally substituted with one or more groups independently selected from halo, nitro, cyano, trifluoromethyl, trifluoromethoxy, (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, and amino;
or a salt thereof.

2. The compound of claim 1, wherein the compound is

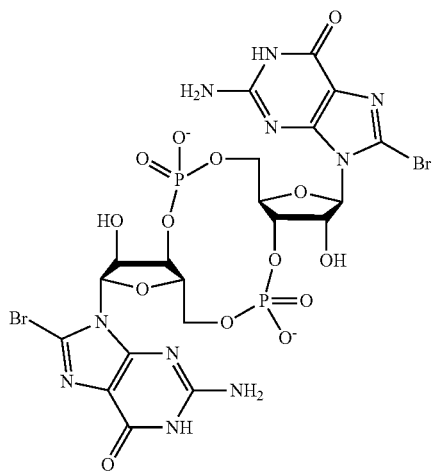

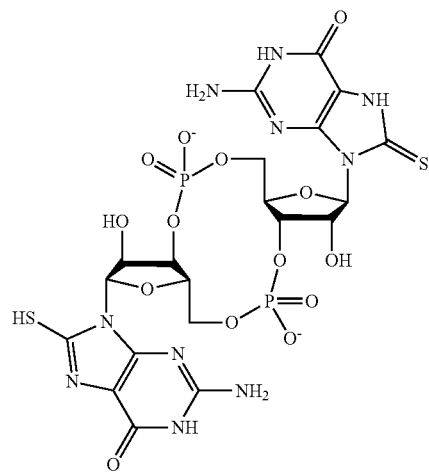

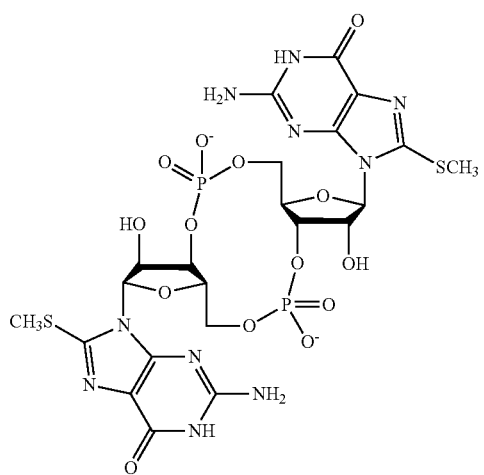

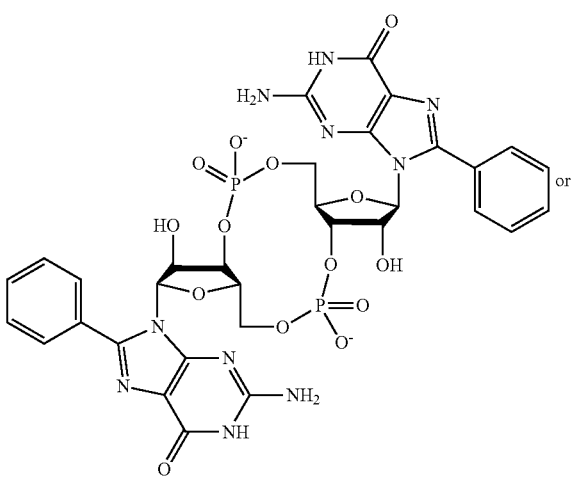

or

-continued
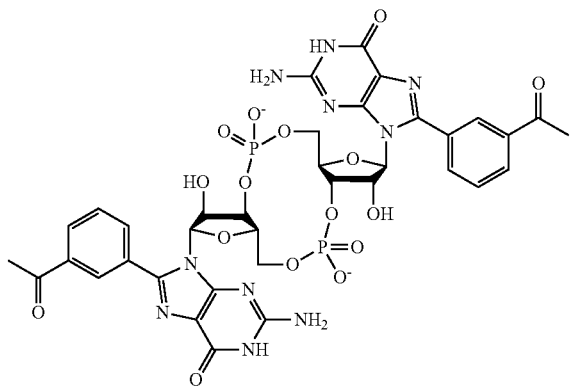
or a salt thereof.
3. The compound of claim 2, wherein the compound is
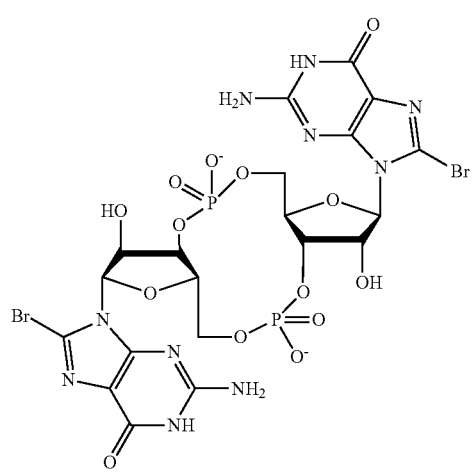
or a salt thereof.
4. The compound of claim 2, wherein the compound is
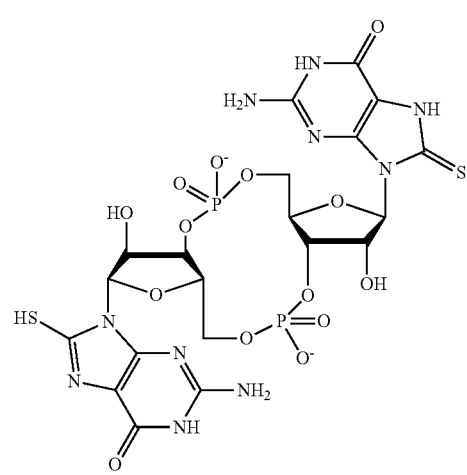
or a salt thereof.
5. The compound of claim 2, wherein the compound is
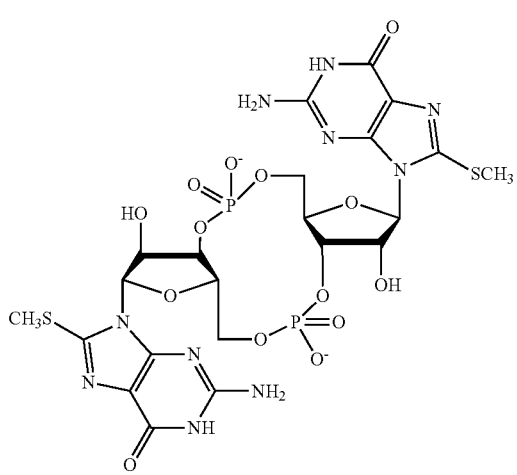
or a salt thereof.
6. The compound of claim 2, wherein the compound is
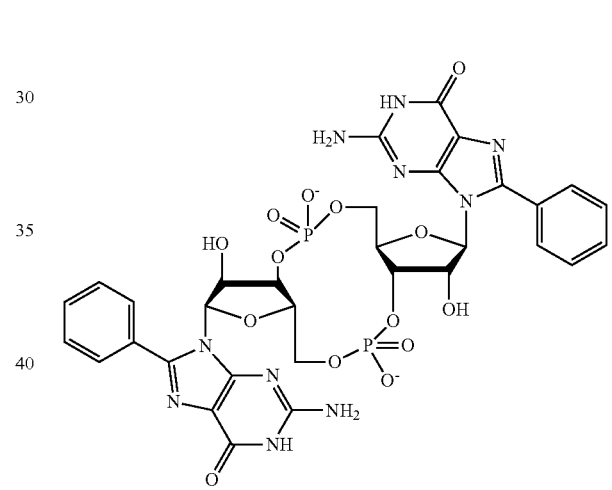
or a salt thereof.
7. The compound of claim 2, wherein the compound is
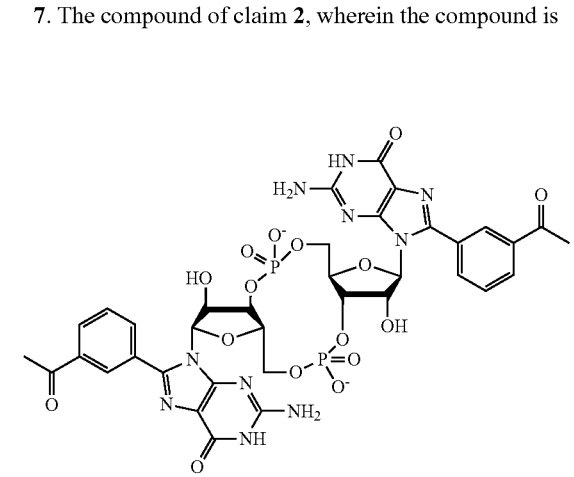
or a salt thereof.

8. The compound of claim 1, which is a potassium, sodium or lithium salt of the compound.

9. The compound of claim 8, which is a potassium salt of the compound.

10. The compound of claim 3, which is a potassium salt of the compound.

11. A composition comprising a compound as described in claim 1, or a salt thereof, and an acceptable carrier.

12. The composition of claim 11, which is a pharmaceutical composition that comprises a compound as described in claim 1, or a salt thereof, and a pharmaceutically acceptable carrier.

13. The composition of claim 11, which comprises a bimolecular, tetramolecular or octamolecular complex of the compound as described in claim 1, or a salt thereof.

14. The composition of claim 13, which comprises a bimolecular complex of the compound as described in claim 1, or a salt thereof.

15. The composition of claim 13, which comprises a tetramolecular complex of the compound as described in claim 1, or a salt thereof.

16. The composition of claim 13, which comprises an octamolecular complex of the compound as described in claim 1, or a salt thereof.

17. A composition comprising a compound as described in claim 2, or a salt thereof, and an acceptable carrier.

18. The composition of claim 17, which is a pharmaceutical composition that comprises a compound as described in claim 2, or a salt thereof, and a pharmaceutically acceptable carrier.

19. A method for synthesizing the compound as described in claim 3, comprising converting a compound of formula 1

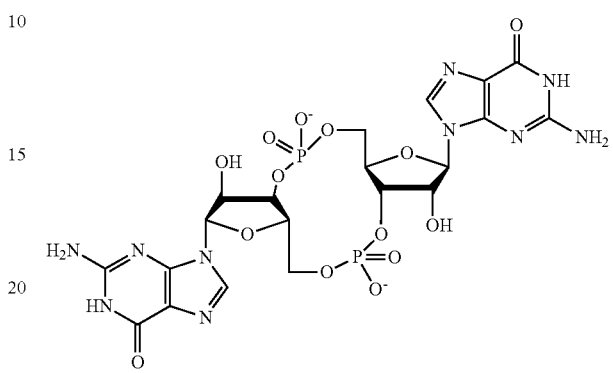

to the compound as described in claim 3.

* * * * *